United States Patent [19]

Messerschmidt

[11] Patent Number: 4,712,912

[45] Date of Patent: Dec. 15, 1987

[54] SPECTROPHOTOMETRIC IMAGE SCRAMBLER FOR FULL APERTURE MICROSPECTROSCOPY

[75] Inventor: Robert G. Messerschmidt, Westport, Conn.

[73] Assignee: Spectra-Tech, Inc., Stamford, Conn.

[21] Appl. No.: 837,672

[22] Filed: Mar. 10, 1986

[51] Int. Cl.$^4$ .................. G01N 21/55; G01N 21/59
[52] U.S. Cl. ........................... 356/73; 356/300; 356/346; 356/445
[58] Field of Search ............. 356/73, 300, 303, 319, 356/320, 323, 324, 325, 330, 346, 445, 447, 448

[56] References Cited

U.S. PATENT DOCUMENTS

| | | |
|---|---|---|
| 2,766,653 | 10/1956 | Martin et al. ............. 356/448 |
| 3,913,872 | 10/1975 | Weber . |
| 4,054,364 | 10/1977 | Webster . |
| 4,382,656 | 5/1983 | Gilby . |
| 4,481,418 | 11/1984 | Vanzetti et al. . |
| 4,519,707 | 5/1985 | Kuffer . |

FOREIGN PATENT DOCUMENTS 0062322  5/1980  Japan ......................... 356/319

OTHER PUBLICATIONS

Walter G. Driscoll and William Vaughan, *Handbook of Optics*, 2-54,55 (1978).

Digilab Micro/FI-IR Users Newsletter, vol. 2, No. 1, Jan. 1986.

*Primary Examiner*—F. L. Evans
*Assistant Examiner*—Fred Samuels
*Attorney, Agent, or Firm*—Kenyon & Kenyon

[57] ABSTRACT

The optical system of the present invention comtemplates directing a beam of radiant energy to either an aperture beam splitter or polarizing beam splitter. Radiant energy from the beam splitter forms a first remote image at an entrance to an image scrambler so that any image information which the beam contains is destroyed. The output of the scrambler fills the full aperture of a focusing objective that reproduces the image of the output of the scrambler onto a sample. A mask, positioned at a remote image between the output of the scrambler and focusing objective, determines the geometrical shape of the sample image. The focusing objective images the radiant energy that is reflected from the sample to a second remote image at the scrambler so that the scrambler destroys image information while retaining spectroscopic information. The beam splitter reflects a portion of the radiant energy from the scrambler to the detector. The absence of image information in the radiant energy from the sample reduces measurement errors by producing a predictable dispersion of radiant energy at the detector.

25 Claims, 6 Drawing Figures

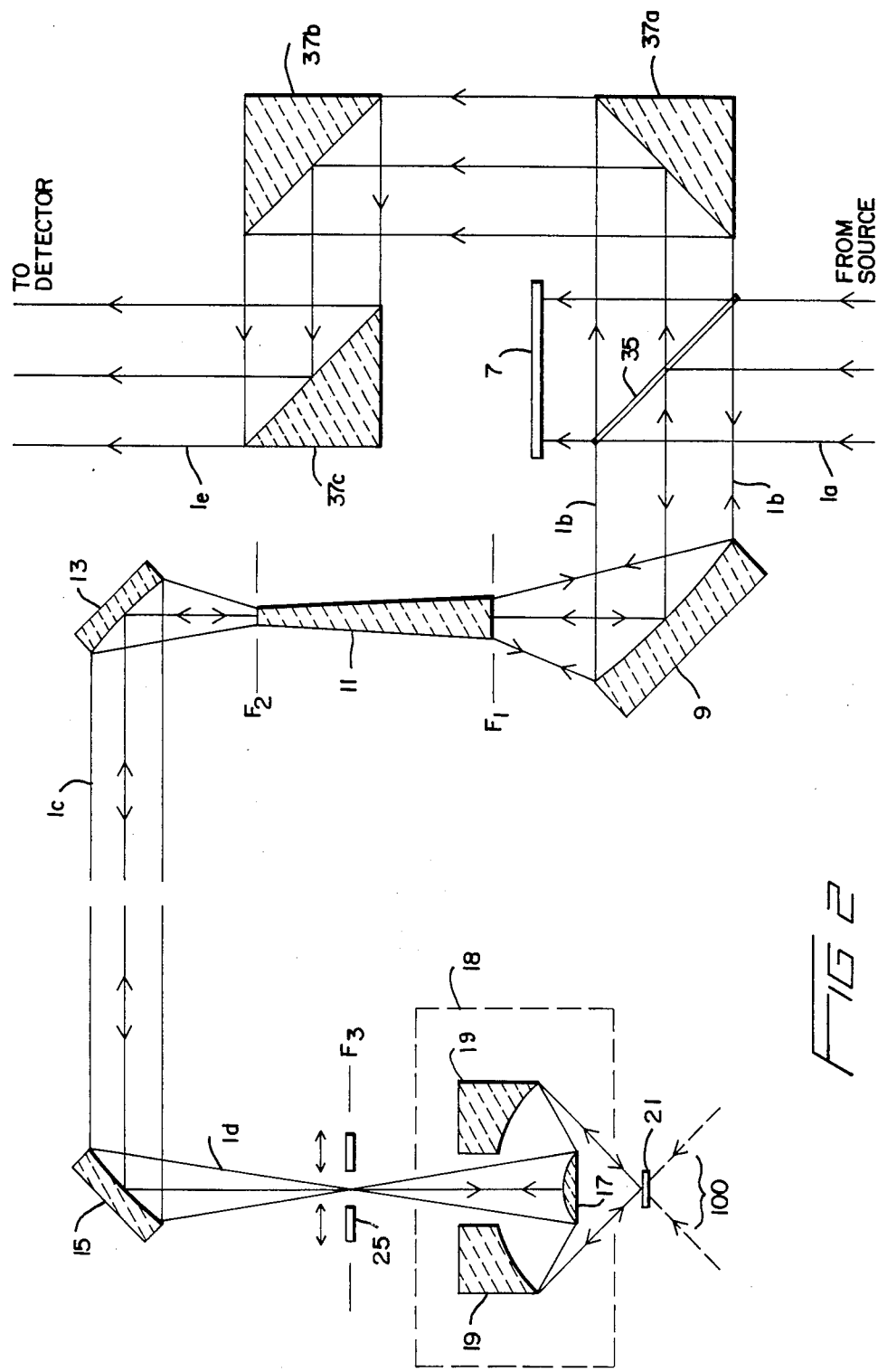

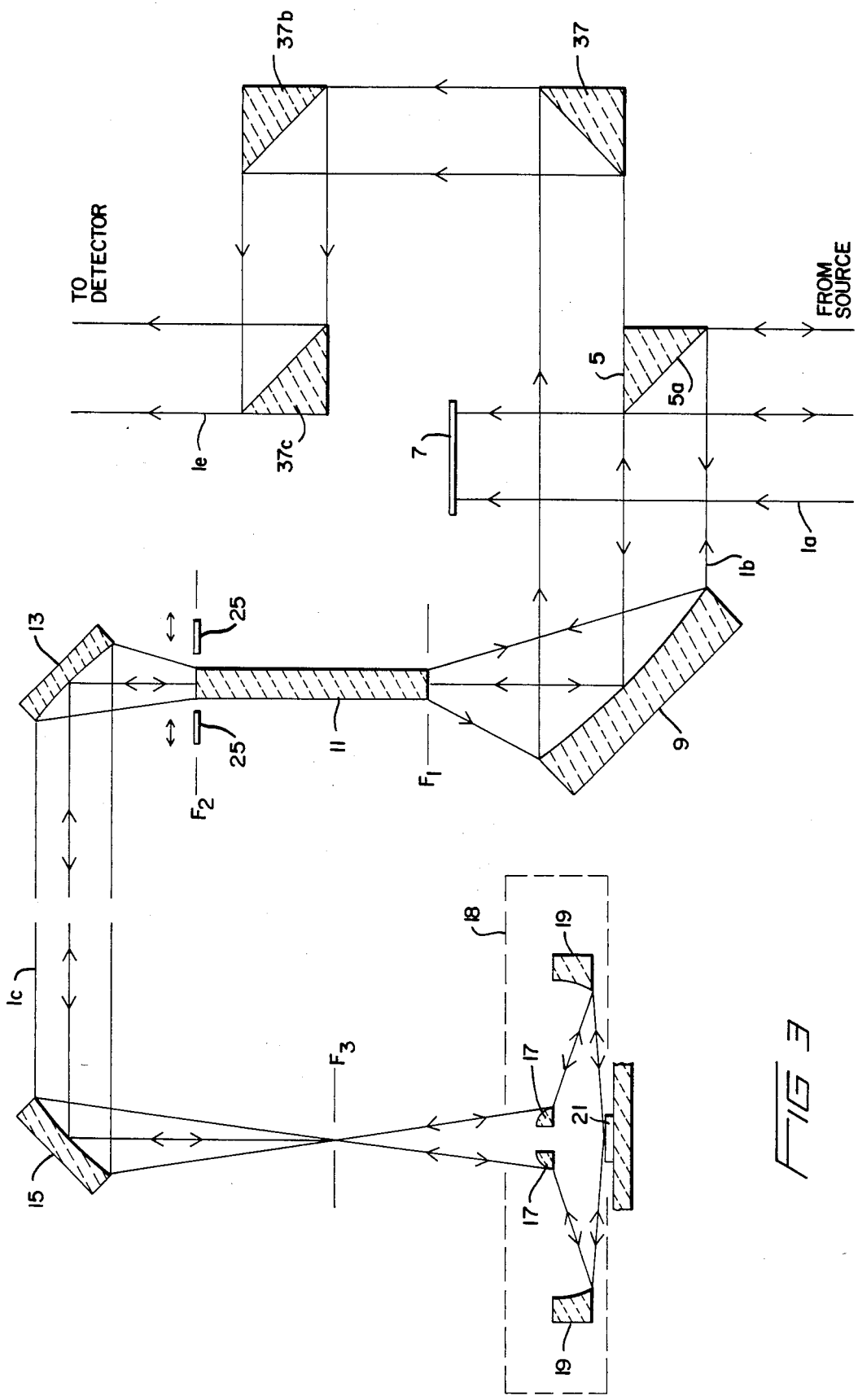

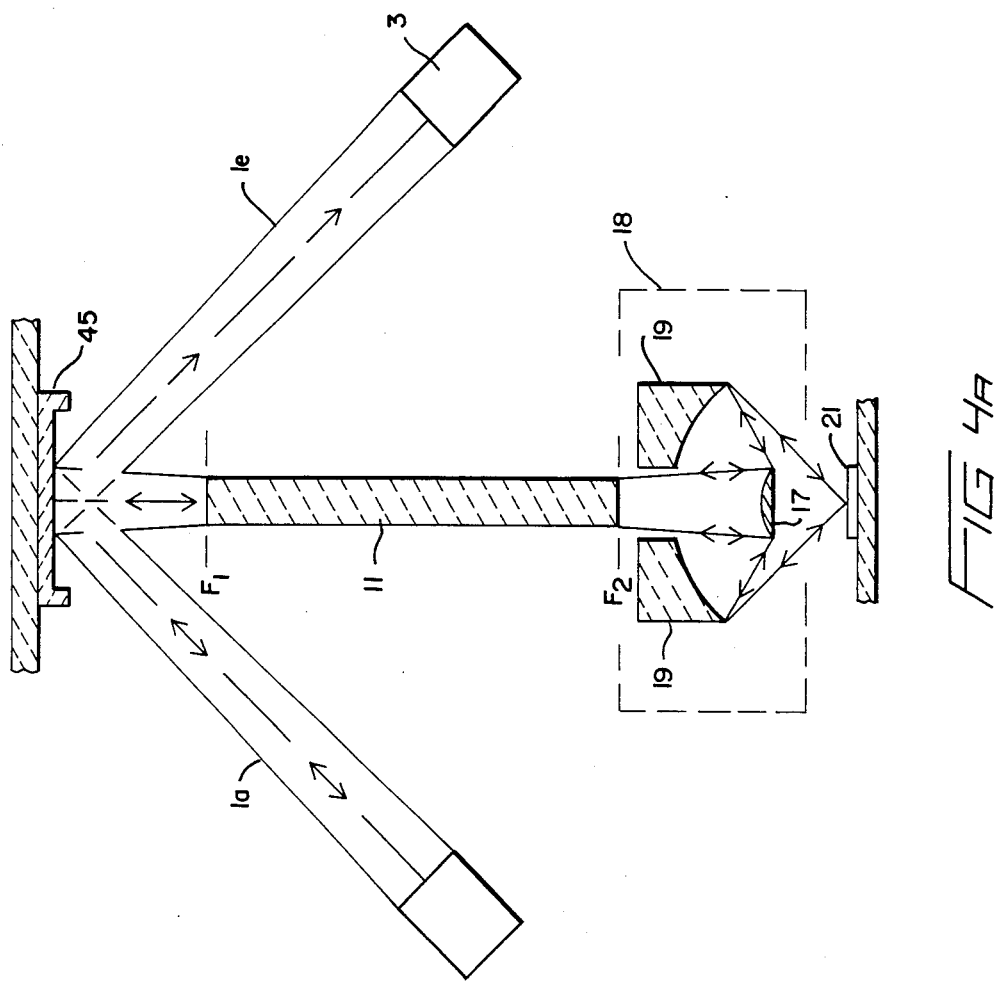
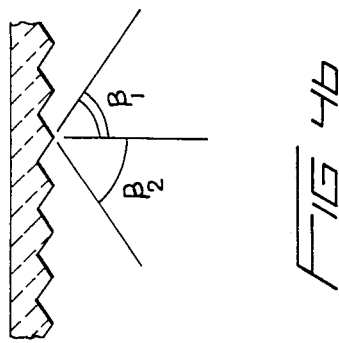
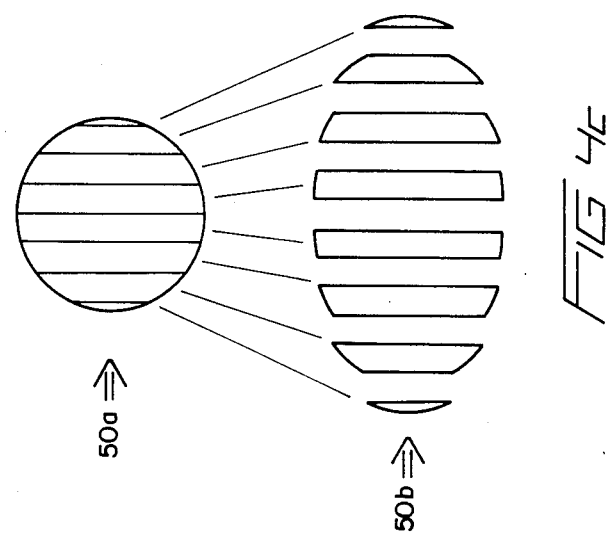

SPECTROPHOTOMETRIC IMAGE SCRAMBLER FOR FULL APERTURE MICROSPECTROSCOPY

BACKGROUND OF THE INVENTION

1. Field of the Invention.

The present invention relates to a method and apparatus for redistributing radiant energy from an image formed in a spectrophotometer to obtain more accurate spectroscopic measurements of selected areas of a sample.

2. Description of Related Art.

Known beam splitters may be divided into three classes. The first class is an amplitude beam splitter which typically uses a partially reflecting/partially transmitting element to split the amplitude of an incident wave front. A common example of an amplitude beam splitter used at optical wavelengths is a partially silvered mirror. The beam splitter reflects a first portion of the radiant energy and transmits a second portion. Typically a portion of either the transmitted or reflected energy is utilized in an optical system and returned to the beam splitter where the beam splitter transmits a third portion and reflects a fourth portion of the radiant energy. It is known to maximize the efficiency of an amplitude beam splitter by transmitting and reflecting equal amounts of the radiant energy that is incident to the beam splitter. Thus, the maximum efficiency at which radiant energy may be transmitted is one half of one half of the incident radiant energy, or 25 percent. Further, the transmissive and reflective properties of an amplitude beam splitter should not change with the wavelength of the incident radiant energy if the beam splitter is used in spectroscopic applications.

In many spectroscopic applications, however, an ideal amplitude beam splitter does not exist. For example, a common amplitude beam splitter used in infrared spectroscopy is a film of germanium on a potassium bromide substrate. This type of amplitude beam splitter is expensive and not very durable. Further, a film of germanium does not produce a perfect division of energy, and its reflective/transmissive properties change greatly with wavelength at infrared wavelengths.

A second class of beam splitter is an aperture beam splitter. An aperture beam splitter involves inserting at least one intercepting mirror into a beam of radiant energy at some point along its optical path. An aperture beam splitter is reliable and easily fabricated so as to exhibit perfect reflectivity over a large range of potential wavelengths because many reflecting surfaces are known that exhibit near total reflection at wavelengths of interest. An aperture beam splitter, however, reduces the effective aperture of the optical system because the intercepting mirror reflects only a portion of the beam of radiant energy. Any reduction in aperture is undesirable for microspectrometry because a larger aperture can resolve a smaller object.

A third class of beam splitter uses a polarizer such as a wire grid or Brewster's plate. Polarizers are known that exhibit near perfect 50 percent transmission or reflection provide for full utilization of existing aperture and are reliable. A disadvantage to using a polarizing beam splitter, however, is that it illuminates the sample with only radiant energy having a particular polarization. Restricting observation to one particular polarization is undesirable for some applications because the spectrum of a sample may change at different polarizations. Further, much reflected radiant energy may be lost if the polarization is mismatched to a sample that is bifringent; e.g. if the incident radiant energy has predominantly one type of polarization and the sample reflects radiant energy with predominately the opposite polarization.

It is known that the response of detectors for commercial infrared spectrophotometers changes depending on how much of the total surface area of the detector is illuminated. For example, mercury cadmium telluride detectors, typically used in commercial FT-IR spectrophotometers, give rise to "beat patterns" when partially illuminated due to phenomena that are completely unrelated to the spectrum of the sample such as multiple internal reflectance within the detector. Obtaining a spectrum with a spectrophotometer typically involves taking a "baseline" measurement of the source by fully illuminating the detector. The spectrophotometer does not compensate for distortions produced by the detector if the detector is illuminated differently during the baseline measurement than during the spectroscopic measurement of the sample.

Irregular illumination of the detector is produced in several ways. For example, directly imaging the sample onto the detector may produce uneven illumination because of the image properties of the sample. Even more drastic changes in the illumination of the detector results when the sample is masked to limit the geometric size of the illuminated area on the sample. Often the shape of the mask combines with the image of sample at the detector to produce uneven illumination. Moreover, the foregoing irregularities in the illumination of the detector cannot be produced independent of taking the spectral measurement and therefore may not be compensated for in the baseline measurement.

Any image information contained in an image may be destroyed by forming the image at one end of a light pipe. Radiant energy diverges from the image focus and reflects off the walls of the light pipe at different locations depending on the divergence of each segment of the radiant energy beam, thus spreading the radiant energy from different portions of the image throughout the volume of the light pipe so that the image information originally contained in the image is destroyed. The radiant energy emerges from the light pipe as if from a focus that contains only an image of a homogeneous distribution of radiant energy.

It is further known in the art to employ a light pipe before the detector of a spectrophotometer to scramble an image and evenly spread the radiant energy across the entire surface of the detector and that destruction of the image information contained in the sample does not result in loss of spectroscopic information contained in the radiant energy.

SUMMARY OF THE INVENTION

The present invention relates to an optical system that obtains the benefits of an aperture or polarizing beam splitter without reducing effective aperture or introducing unwanted polarization into the incident radiant energy. Further, the present invention eliminates unpredictable irregularities caused by forming the image of a sample or other inhomogeneous source of radiant energy on a detector.

The optical system of the present invention contemplates directing a beam of radiant energy to either an aperture beam splitter or polarizing beam splitter. Radiant energy from the beam splitter forms a first remote image at an entrance to an image scrambler so that any image information which the beam contains is destroyed. The output of the scrambler fills the full aperture of a focusing objective that reproduces the image of the output of the scrambler onto a sample. A mask, positioned at a remote image between the output of the scrambler and focusing objective, determines the geometrical shape of the sample image. The focusing objective images the radiant energy that is reflected from the sample to a second remote focus at the scrambler so that the scrambler destroys image information while retaining spectroscopic information. The beam splitter reflects a portion of the radiant energy from the scrambler to the detector. The absence of image information in the radiant energy from the sample reduces measurement errors by producing a predictable dispersion of radiant energy at the detector.

The present invention contemplates several embodiments for obtaining better microspectroscopic performance. An aperture beam splitter, such as an intercepting mirror or island splitter, or a reflective polarizer may be inserted into a segment of the optical path of a beam of radiant energy. The reflected radiant energy forms a remote image at the entrance to an image scrambler comprising a light pipe. A focusing objective forms an image of the radiant energy emerging from the light pipe. The light pipe is positioned so that the radiant energy completely fills the field of view of the focusing objective. A mask is positioned between the light pipe and focusing objective to determine the geometric shape of the image formed on the sample. Radiant energy is reflected from the sample back to the light pipe so that any image optical information relating to the sample or mask is destroyed in the light pipe. The intercepting mirror reflects a portion of the radiant energy from the light pipe to a detector.

The present invention may be used in a transmissive mode. Radiant energy may be directed through a sample and collected by a focusing objective. The image of the sample may be reformed at a remote location and masked. The image optical information about the sample and mask is destroyed in the light pipe so that the detector receives only spectroscopic information about the sample.

A facet beam splitter that functions as an aperture beam splitter may permit as much as one half of the incident radiant energy to be received by the detector. Further, a tapered light pipe may be used as an image scrambler so as to change the geometric shape, energy density or effective focal length of the optical system.

BRIEF DESCRIPTION OF THE DRAWINGS

FIG. 2 is a schematic illustration of an embodiment of the present invention using a polarizing beam splitter in either a reflectance or transmission mode in combination with an image scrambler that changes the effective focal length of the system;

FIG. 3 is a schematic illustration of an alternate method of using an aperture beam splitter in combination with a grazing angle microscope objective; and FIG. 4a is a schematic illustration of an embodiment of the present invention using a facet beam splitter; FIG. 4b shows an enlargement of the facet beam splitter; and FIG. 4c illustrates image distortion caused by the facet beam splitter.

DETAILED DESCRIPTION OF THE PREFERRED EMBODIMENTS

Figure 1:
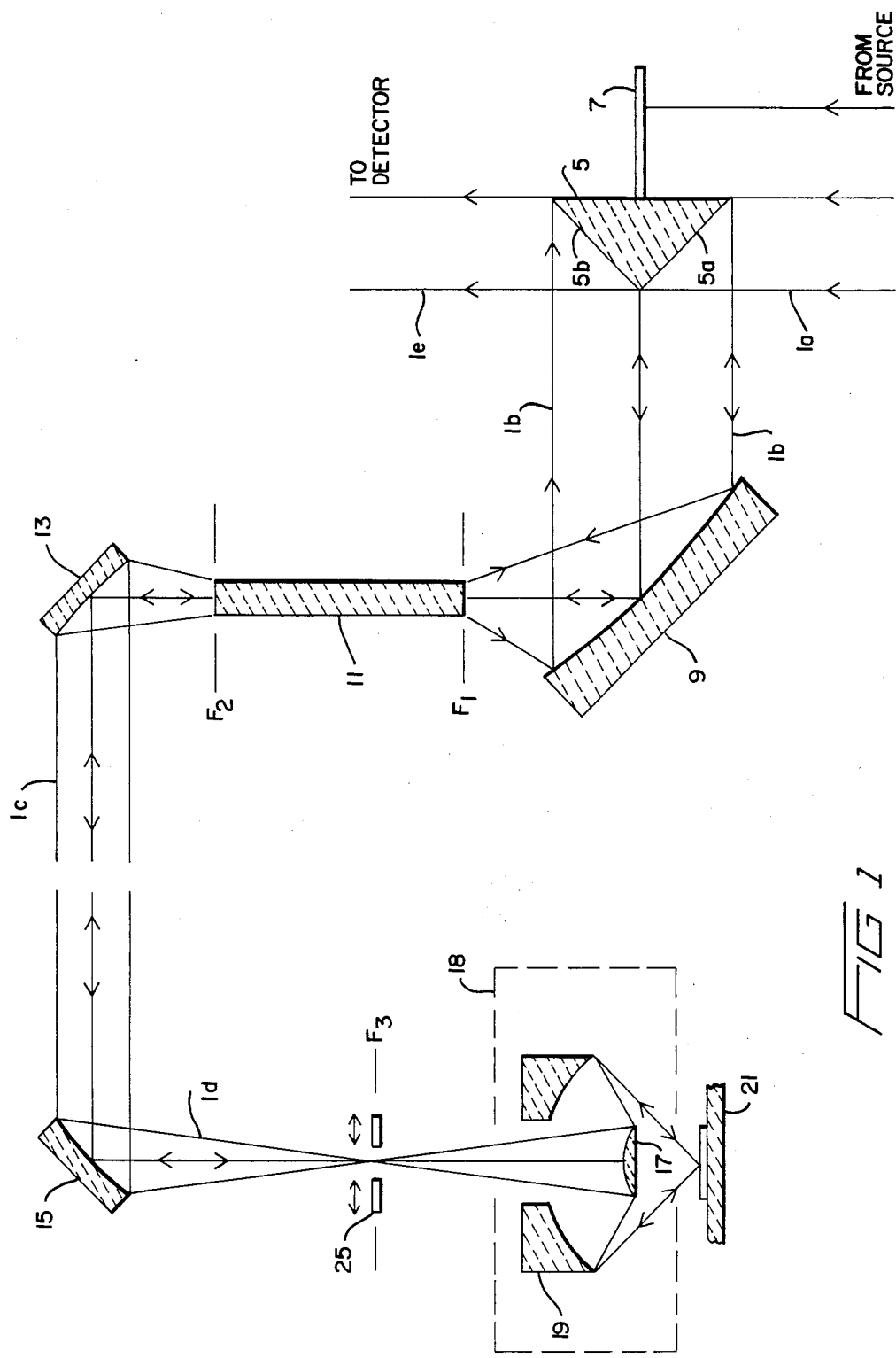
FIG. 1 is a schematic illustration of an embodiment of the present invention that uses an aperture beam splitter.

Referring to FIG. 1, a beam of radiant energy $1a$ from a source, not shown, falls on intercepting mirror 5 and stop 7. Mirror surface $5a$ of intercepting mirror 5 reflects a segment $1b$ of incident energy beam $1a$ to right angle ellipsoidal mirror 9. Stop 7 prevents the unused portion of beam $1a$ from reaching the detector. Ellipsoidal mirror 9 forms a remote image of the source at remote image $F_1$.

The incident radiant energy from mirror 9 diverges from image $F_1$ and enters a light pipe 11. Internal walls of the light pipe confine the diverging beam of radiant energy to the internal volume of the light pipe. The effect of introducing the light pipe into the optical path of beam 1 is to scramble the image of the source of the radiant energy. The term "scramble" is indicative of the ability of a light pipe to mix or decorrelate a light beam. As shown in FIG. 1, light pipe 11 scrambles the image of the source of the radiant energy formed at $F_1$ so that the radiant energy emerging at $F_2$ does not contain an image of the source.

As shown in FIG. 1, the remote image formed at $F_2$ corresponds to the focus of a right angle ellipsoidal mirror 13 so that radiant energy from remote image $F_2$ may be directed as beam $1c$ to an arbitrary distance from the source. Right angle ellipsoidal mirror 15 forms a third remote image at $F_3$ corresponding to a replica of the image at $F_2$. Image $F_3$, as modified by mask 25, is imaged by the Cassegrain objective 18 onto sample 21.

Preferably, the geometric shape of the image formed at sample 21 is determined by a mask placed at a remote image. For example, FIG. 1 shows a mask 25 comprising one or more knife edges located at remote image $F_3$. The mask modifies the geometric shape of the image formed at $F_3$ by removing a portion of the radiant energy from the image plane. It is to be appreciated, however, that mask 25 may be positioned at any remote image located between sample 21 and light pipe 11 such as at remote image $F_2$.

In the embodiment of the present invention shown in FIG. 1 the entire aperture of mirrors 17 and 19 forms and receives an image of sample 21. The incident and reflected energy occupies the same physical space in the Cassegrain objective 18. Thus, the optical system shown in FIG. 1 utilizes the full aperture of the Cassegrain objective while also obtaining the greater efficiency and accuracy inherent in using an aperture beam splitter.

Light pipe 11 may comprise a hollow metallic light conduit having inside reflective surfaces to cause multiple specular reflection of the radiant energy. Alternately, light pipe 11 may comprise a solid rod of refractive material capable of producing total internal reflection. The light pipe is chosen to produce the desired amount of scrambling of the relevant images. For purposes of the present invention it is sufficient to understand that the extent to which an image is scrambled is proportional to the number of internal reflections of the radiant energy in the light pipe. The selection of the type and shape of the light pipe is a design criterion that depends primarily on the desired number of internal reflections. A hollow light pipe that relies on specular reflection causes a reduction in the intensity of the radiant energy at each reflection. In contrast, an internal reflection rod does not decrease the radiant energy at each internal reflection in the light pipe but does produce a reduction in the total energy each time the radiant energy enters or exits the rod. Thus, an internal reflectance rod is preferable for applications requiring greater scrambling of an image.

The radiant energy reflected from sample 21 returns along the optical paths represented by 1d and 1c in FIG. 1 so that ellipsoidal mirror 13 forms an image of the sample and mask at remote image $F_2$. The image content of remote image $F_2$, however, is destroyed in light pipe 11 as previously described in connection with remote image $F_1$. Thus, the reflected radiant energy that travels back along optical path 1b to mirror 5 contains only spectroscopic information about the sample. Reflective surface 5b of intercepting mirror 5 directs half of the reflected radiant energy to a detector, not shown.

It is significant to the present invention that neither the image characteristics of the sample nor the mask are imaged onto the detector. The embodiment of the invention shown in FIG. 1, moreover, destroys both the image of the source, sample and mask in a single light pipe so that spectroscopic measurements can be taken without interference from extraneous image information carried by the radiant energy while fully filling the aperture of focusing objective 18. The light pipe 11 effectively spreads the radiant energy evenly over half of the surface of the detector. It is to be appreciated that some interference may arise from illuminating only half of the detector. However, the magnitude of the distortions produced by illuminating only half of the detector is substantially less than that resulting from imaging the mask and sample onto the detector. Further, any irregularities produced by evenly illuminating half of the detector are relatively predictable and may be eliminated by leaving a stop 7 in the optical path when making the baseline measurement. Alternately, the entire surface of the detector may be illuminated by inserting an additional light pipe along path 1e between the detector and mirror surface 5b of intercepting mirror 5.

FIG. 2 shows the present invention used in combination with a polarizing beam splitter. The optical path taken by the radiant energy between polarizer 35 and sample 21 is essentially the same as in FIG. 1. Mirrors 37a-37c direct radiant energy from the sample to the detector.

The present invention overcomes many disadvantages associated with polarizing beam splitters by employing an image scrambler. Light pipe 11 effectively depolarizes incident beam 1b so that the radiant energy in beam 1d incident to sample 21 is not polarized. Conversely, the reflected energy transmitted by polarizer 35 may be selected to correspond to the optimal sensitivity of the detector. Some detectors, particularly ones responsive to infrared radiation, are more sensitive to radiant energy having a particular polarization. Thus, the efficiency of the present invention can be enhanced by rotating the polarizing filter to correspond to the maximum sensitivity of the detector.

The embodiment of the present invention shown in FIG. 2 has the further advantage that the radiant energy of beam 1e fills the entire detector, thus eliminating any distortions that may result in using only half the detector surface. The embodiment of the invention shown in FIG. 2 probably does not require the use of an additional scrambling before the detector. Further, any irregularities introduced into the spectrum by the polarizer may be compensated for in obtaining the baseline measurement by leaving the polarizer in place when making the baseline measurement.

FIG. 2 shows two additional modifications of the present invention. Specifically, light pipe 11 is tapered so as to change the effective focal length of the optical system. Radiant energy proceeding from remote image $F_1$ to remote image $F_2$ is compressed so that the focal length of the system increases and the energy density of remote image $F_2$ increases. The increased focal length produces a higher magnification from the same focusing objective 18. Conversely, the radiant energy returning from the sample is decreased in effective focal length by light pipe 11 so that the optical performance of the embodiment shown in FIG. 2 is essentially the same as that for the embodiment shown FIG. 1. Any tapered light pipe, however, may back reflect some of the incident radiant energy, thus decreasing the efficiency of the optical system and permitting some radiant energy to pass directly from the source to the detector. The phenomena of back reflection in tapered light pipes is known and need not be discussed further.

FIG. 2 also illustrates the use of the present invention in a transmissive mode. A beam 100 is shown traveling directly from the source and entering sample 21 from below so as to pass through the sample and be collected by primary mirror 19. In this embodiment, light pipe 11 scrambles the radiant energy being transmitted to the detector. Polarizer 35 may be removed for using the system in a transmissive mode.

Finally, polarizer 35 may be replaced by an island beam splitter. An island splitter comprises a series of small reflective surfaces disposed on a transmissive backing. An island splitter behaves as an aperture splitter so long as the individual reflective surfaces have a size that is comparable to or greater than the wavelength of the incident radiant energy. The effect of substituting an island beam splitter for polarizer 35 in FIG. 2 is that the radiant energy that reaches the detector along beam 1e is not polarized. A second light pipe may be placed along path 1e to prevent the detector from receiving a speckled or motley image caused by the radiant energy passing through the island splitter a second time.

FIG. 3 shows another embodiment of the present invention, wherein the intercepting mirror 5 of FIG. 1 is replaced by an intercepting mirror having only a single reflective surface 5a. Mask 25 is illustrated as located at remote image $F_2$. Finally, mirrors 17 and 19 are illustrated as forming a modified Cassegrain objective 18 suitable for obtaining grazing angles of incidence and reflection from sample 21.

FIG. 4 shows another embodiment of the present invention that uses a facet beam splitter. Referring to FIG. 4a, a beam of radiant energy 1a from source 2 is incident to facet beam splitter 45. FIG. 4b shows a side profile of the reflective surface of facet splitter 45. The facet beam splitter shown in FIG. 4b is an aperture beam splitter so long as the spacing between facets is greater than the wavelength of radiant energy. Radiant energy is reflected from the facet beam splitter to form a remote image at $F_1$. This image is scrambled in light pipe 11 so as to be focused onto sample 21 by mirrors 17 and 19. The reflected radiant energy forms an image of the sample at remote image $F_2$. This remote image is scrambled by light pipe 11 and directed incident to facet splitter 45. The facet splitter divides the beam of reflected radiant energy into two portions, one of which goes to detector 3 as a beam of radiant energy 1e.

The embodiment of the invention shown in FIG. 4a enables the facet splitter to direct fully one half of the radiant energy contained in beam 1a to the detector 3. Referring to FIG. 4b, the angle of incidence of the incident energy beam 1a to the facet splitter is shown as angle $\phi$. The angle formed by each individual facet is shown in FIG. 4b as angle $\beta$ and is measured normal to the facet splitter. It can be shown that all the radiant energy in incident beam 1a can be reflected into light pipe 11 without vignetting the final image if the angle of incidence, $\phi$, corresponds to 22.5° and the facet angle for the incident radiation, $\beta_1$, corresponds to 67.5°. Further, the beam of reflected energy will split exactly in half if the facet angle for the reflected radiant energy, $\beta_2$, also corresponds to 67.5° so that beam 1e may contain as much as one half of the radiant energy present in incident beam 1a.

It is to be appreciated, however, that facet splitter 45 distorts remote image $F_1$ as shown in FIG. 4c. Image 50a corresponds to the image that would be formed but for the presence of the facet splitter in the optical path. Image 50b corresponds to the distorted image formed at remote image $F_1$ by facet splitter 45. As shown, each individual facet reflects segments of the radiant energy to the remote image. In between each segment of the beam, however, is an area that does not contain radiant energy from the source. The effect of facet splitter 45 is to form a distorted image that takes on the general appearance of a fringe pattern.

Light pipe 11 destroys the distortion shown in FIG. 4c as 50b. The entrance aperture of light pipe 11, however, must have a greater diameter than in the other embodiments because remote image $F_1$ is larger due to the distortions introduced by the facet splitter. The larger image area reduces the energy density at secondary mirror 17 and, ultimately, the energy density at sample 21. Also, the size of mirror 17 may need to be increased to accommodate the larger diameter of the energy beam or some radiant energy will not be focused onto sample 21.

The tendency of the facet splitter to enlarge the image area for the embodiment of the invention shown in FIG. 4a may be mitigated for example, a tapered light pipe. Light pipe 11 could have an entrance face at remote image $F_1$ corresponding to the approximate contour of the outer envelope of the distorted image shown in FIG. 4c as 50b. The light pipe could taper down at $F_2$ to correspond in size to an undistorted image shown as 50a. A tapered light pipe, however, may lose some radiant energy due to back reflection. Thus, the greater throughput of radiant energy obtained by using a facet splitter is at least partially offset by the lower energy density obtained at remote image $F_1$.

The principles, preferred embodiments and modes of operation of the present invention have been described in the foregoing specification. The invention which is to be protected herein should not, however, be construed as limited to the particular forms described, as these are to be regarded as illustrative rather than restrictive. Variations and changes may be made by those skilled in the art without departing from the spirit of the invention. Accordingly, the foregoing detailed description should be considered exemplary in nature and not as limiting to the scope and spirit of the invention set forth in the appended claims.

What is claimed is:

1. An optical system for a spectrophotometer that has a source of a beam of radiant energy and a detector for the radiant energy, said optical system directing radiant energy from the source to a sample along an optical path, comprising:
   means for scrambling the beam of radiant energy from the source said scrambling means being positioned to scramble a segment of the radiant energy from the source;
   means for forming a sample image with the scrambled radiant energy from the source;
   means for collecting radiant energy reflected from the sample, said radiant energy having image information about the sample;
   said means for scrambling being positioned to also scramble said reflected radiant energy to destroy said sample image; and
   means for directing said scrambled reflected radiant energy to the detector.

2. An optical system as claimed in claim 1, further comprising:
   means for forming a first remote image with the segment of radiant energy from the source between the source and scrambling means along said optical path so that said scrambling means destroys said first image;
   means for forming a second remote image with said scrambled radiant energy from the source; and
   said means for forming the sample image forms an image corresponding to said second remote image at the sample.

3. An optical system as claimed in claim 2, further comprising means for masking said second remote image so that said sample image includes an image of said masking means.

4. An optical system as claimed in claim 2, further comprising a beam splitter positioned between the source and said scrambling means along the optical path, said scrambling means destroying any image imposed on the source by the beam splitter, said beam splitter directing a segment of the radiant energy from the source to the sample.

5. An optical system as claimed in claim 4, wherein:
   said means for forming the sample image forms an image of the sample at the second remote image with radiant energy reflected from the sample;
   said scrambling means being positioned to destroy said sample image; and
   said beam splitter being positioned to reflect a portion of said reflected radiant energy to the detector.

6. An optical system as claimed in claim 5, wherein the radiant energy from the source and said reflected radiant energy are superimposed in space.

7. An optical system as claimed in claim 5, wherein said beam splitter comprises a facet splitter, said facet splitter having facets that are spaced apart by an average distance that is greater than the wavelength of the incident radiant energy, each of said facets having an incident and reflective face.

8. An optical system as claimed in claim 7, wherein said incident face of said facets form an angle of substantially 67.5° relative to a normal to the facet splitter; and
   said reflective face of said facets form an angle of substantially 67.5° relative to a normal to the facet splitter.

9. An optical system as claimed in claim 7, further comprising means for condensing the radiant energy from the source after it is reflected from said reflective face of said facets.

10. An optical system as claimed in claim 9 wherein said means for condensing the radiant energy comprises a tapered light pipe, said tapered light pipe having first and second ends positioned at said first and second remote images, respectively, said first end having a larger cross sectional area than said second end.

11. An optical system as claimed in claim 5, wherein said beam splitter comprises an intercepting mirror positioned to intercept half of the beam of radiant energy from the source.

12. An optical system as claimed in claim 5, wherein said beam splitter comprises a polarizing screen.

13. An optical system as claimed in claim 5, wherein said beam splitter comprises an island splitter, said island splitter having reflective surfaces that have an average size that is comparable to or greater than the wavelength of the radiant energy.

14. An optical system as claimed in claim 5, wherein said means for forming said sample image comprises means for directing the radiant energy from the source to the sample at grazing angles and receiving radiant energy reflected from the surface at grazing angles.

15. An optical system as claimed in claim 2, wherein said means for scrambling the radiant energy comprises a light pipe having first and second ends, said first end being positioned at said first remote image so that the radiant energy diverging from said first image reflects from the sides of said light pipe; and said second end being positioned at said second image focus to scramble the radiant energy reflected from the sample.

16. An optical system as claimed in claim 15, wherein said light pipe comprises a total internal reflectance crystal.

17. An optical system as claimed in claim 15, wherein said light pipe comprises reflective surfaces arranged to form a hollow inner chamber, said reflective surfaces specularly reflecting radiant energy.

18. An optical system as claimed in claim 1, wherein said means for collecting radiant energy emitted from the sample is positioned to collect radiant energy that is transmitted through the sample.

19. A method for obtaining a spectrum with a spectrophotometer that has a source of a beam of radiant energy and a detector for the radiant energy, including the steps of directing radiant energy from the source to a sample along an optical path, comprising the steps of:
scrambling a segment of the beam of radiant energy from the source;
forming a sample image with the scrambled radiant energy from the source;
collecting radiant energy reflected from the sample, said radiant energy having image information about the sample;
scrambling said reflected radiant energy to destroy said sample image; and
directing said scrambled radiant energy to the detector.

20. The method as claimed in claim 19, wherein the step of forming the sample image further comprises the steps of:
forming a first remote image with the segment of radiant energy from the source between the source and scrambling means along said optical path so that said scrambling means destroys said first image;
forming a second remote image with said scrambled radiant energy from the source; and
forming an image at the sample corresponding to said second remote image.

21. The method as claimed in claim 20, further comprising the step of masking said second remote image so that said sample image includes an image of said masking means.

22. The method as claimed in claim 20 further comprising the steps of directing a segment of the radiant energy from the source to the sample with a beam splitter, said beam splitter being positioned betwen the source and scrambling means so that the scrambling means destroys any image imposed on the source by the beam splitter.

23. The method as claimed in claim 20, further comprising the steps of:
forming the sample image at the second remote image with radiant energy reflected from the sample;
scrambling said sample image; and
reflecting a portion of said emitted radiant energy to the detector with a beam splitter.

24. The method as claimed in claim 23, wherein said radiant energy from the source and said reflected radiant energy from the sample are superimposed in space.

25. The method as claimed in claim 20 further comprising the steps of:
directing of radiant energy to a bottom surface of the sample to form said sample image; and
collecting radiant energy that is transmitted through the sample and emitted from a top surface of the sample.

* * * * *